United States Patent [19]

Haniff et al.

[11] Patent Number: 5,491,261
[45] Date of Patent: Feb. 13, 1996

[54] POLY-PERFLUOROALKYL-SUBSTITUTED ALCOHOLS AND ACIDS, AND DERIVATIVES THEREOF

[75] Inventors: Marlon Haniff, West Orange, N.J.; Robert Falk, New City, N.Y.; Ted Deisenroth, Carmel, N.Y.; Karl F. Mueller, New York, N.Y.

[73] Assignee: Ciba-Geigy Corporation, Tarrytown, N.Y.

[21] Appl. No.: 270,083

[22] Filed: Jul. 1, 1994

[51] Int. Cl.[6] .................... C07C 43/15; C07C 43/17; C07C 43/10; C07C 43/12; C07C 53/126; C07C 53/02; C07C 55/22; C07C 55/32

[52] U.S. Cl. .................... 562/582; 546/302; 546/246; 560/153; 560/179; 560/180; 560/181; 560/182; 560/183; 560/184; 562/564; 562/567; 562/568; 562/586; 564/203; 564/204; 564/209; 564/442; 564/462; 564/501; 564/504; 568/32; 568/45; 568/46; 568/589; 568/649; 568/674; 568/677

[58] Field of Search .................... 562/564, 567, 562/568, 582, 586; 546/302, 548; 560/153, 179–184; 568/32, 45, 46, 589, 649, 674, 677; 564/203, 204, 209, 442, 462, 501, 504

[56] References Cited

U.S. PATENT DOCUMENTS

| | | | |
|---|---|---|---|
| 3,828,098 | 8/1974 | Gilleo et al. | 568/586 |
| 3,952,066 | 4/1976 | Glickman et al. | 568/46 |
| 3,952,075 | 4/1976 | Nakamura et al. | 562/564 |
| 4,001,305 | 1/1977 | Dear et al. | 568/46 |
| 4,429,162 | 1/1984 | Cooke et al. | 568/46 |
| 4,946,992 | 8/1990 | Falk et al. | 568/674 |
| 5,097,067 | 3/1992 | Jacobson | 562/582 |
| 5,103,048 | 4/1992 | Knaup et al. | 562/568 |
| 5,214,216 | 5/1993 | Tohzuka et al. | 562/586 |
| 5,266,724 | 11/1993 | Kai et al. | 562/567 |

*Primary Examiner*—Joseph E. Evans
*Attorney, Agent, or Firm*—Kevin T. Mansfield

[57] ABSTRACT

Di-, tri- and poly-perfluoroalkyl-substituted alcohols and acids and derivatives thereof are described which are prepared from perfluoroalkyl iodides and di-, tri- or polyallyl alcohols or acids. These compounds contain two or more perfluoroalkyl-iodoalkyl or perfluoroalkyl-alkenyl groups and one or two alcohol or acid groups or derivatized alcohol or acid functions. They can be reacted with isocyanates, epoxy compounds, anhydrides, acids or acid derivatives to prepare a great variety of oil- and water-repellent compositions which are useful for oil- and water-repellent treatment of textiles, glass, paper, leather and other substrates.

18 Claims, No Drawings

POLY-PERFLUOROALKYL-SUBSTITUTED ALCOHOLS AND ACIDS, AND DERIVATIVES THEREOF

BACKGROUND OF THE INVENTION

Perfluoroalkyl-substituted polymers possess free surface energies even lower than that of polytetrafluoroethylene. They have therefore long been used to impart oil- and water repellency to a wide variety of substrates, especially textiles. Additionally, phosphate esters of perfluoroalkyl-substituted alcohols are being used as oil- and water-repellent paper sizing, for instance in paper plates and in food packaging products. For such applications, it is especially important that the paper sizing compound contain at least 2 $R_F$- groups, where $R_F$ is a perfluoroalkyl group. When mono-$R_F$-alcohols are used to esterify phosphoric acid, only the diesters are active oil- and water- repellents; the monoester is too water soluble and, even if retained on the cellulose fiber, reduces water repellency, and the triester is not substantive. Making phosphate diesters in high yield is, however, very difficult in practice; substantial amounts of mono- and triesters are always produced as by-products.

Typical fluorinated mono-alcohols are perfluoroalkyl-alkanols, such as 3-perfluoroalkyl-propene- 2-ol. See J. Fluorine Chem., 20 (3), 313–27 (1982), DE 23 33 935 (1974), DE 22 55 672 (1973) and FR 1 473 451 (1967). Such monofunctional alcohols, while suitable for the preparation of acrylic and methacrylic oil- and water-repellent $R_F$-polymers, are less suitable for the preparation of oil- and water-repellent phosphate esters for reasons given above. Likewise, it is also impossible to prepare oil- and water-repellent sulfuric acid half esters from mono-$R_F$-alcohols since such esters are very water soluble anionic surfactants. For the preparation of oil- and water-repellent polyurethanes it is especially important that the diol contain more than one $R_F$ group.

Using di-$R_F$-alcohols makes it possible to prepare oil- and water-repellent phosphate or sulfate monoester paper sizes, since even a monoester contains two $R_F$-groups. Certain di-$R_F$-diols are described in U.S. Pat. Nos. 3,935,277 and 4,946,992. Said patents describe the synthesis of di-$R_F$-alcohols and diols by reaction of $R_F$-ethylenethiol with halogenated alcohols and diols.

Polyurethanes of di-$R_F$-diols are described in U.S. Pat. Nos. 3,968,066, 4,046,944, 4,054,592 and 4,098,742. Phosphate esters are described in U.S. Pat. Nos. 5,091,550 and 5,132,445. Although the di-$R_F$-phosphates show excellent performance, their synthesis involves many steps and costly intermediates. Similar compounds produced by a more straightforward synthesis route and preferably lacking the thermally unstable thioether linkage would be highly desirable.

It has now been discovered that di-, tri- and poly-perfluoroalkyl-substituted alcohols which fulfill these requirements can be prepared in high yields from perfluoroalkyliodides and di-, tri- or polyallyl alcohols or acids. These compounds have not previously been described. They are useful by themselves or as intermediates for making end products which impart outstanding oil and water repellency to textiles, paper, leather, wood and other substrates.

Sugar derived perfluoroalkenyl substituted polyols have been synthesized earlier, namely from xylitol, galactose, and glucose; see Bull. Soc. Chim. Fr., 872-8 (1989), J. Med. Chem., 33 (4), 1262 (1990) and U.S. Pat. No. 4,985,550. Such polyols, with a hydroxyl functionality of three or more, are not suitable for preparing linear polymer compositions since crosslinking is likely to occur.

DETAILED DISCLOSURE

This invention describes di- tri- and oligoperfluoroalkyl-substituted mono- and dialcohols, mono- and diacids and derivatives thereof, and methods for making them. Other aspects of this invention relate to the reaction products of oligoperfluoroalkyl alcohols with isocyanates, epoxides, acids, acid chlorides, and anhydrides.

Another aspect of this invention relates to a substrate containing 0.01 to 10% by weight of an organofluorine-containing composition, at least part of said fluorine being provided by one or more units derived from an inventive oligoperfluoroalkyl substituted alcohol, acid, or a derivative thereof.

The novel oligo-perfluoroalkyl alcohols and acids are of the formulae I or II

$$(Q_F\text{—}CH_2O)_b\text{—}Y\text{—}(X)_a \qquad (I)$$

or

$$Z_e(\text{—}L\text{—}(U\text{—}OH)_d)_c \qquad (II)$$

wherein $Q_F$ is $Q_{F1}$ or $Q_{F2}$, in which $Q_{F1}$ is $R_FCH_2CHI$— and $Q_{F2}$ is $R_FCH\!\!=\!\!CH$—, and $R_F$ is a monovalent, perfluorinated, alkyl or alkenyl, straight, branched or cyclic organic radical having three to twenty fully fluorinated carbon atoms, which radical can be interrupted by divalent oxygen or sulfur atoms, with each $R_F$ radical being identical or different from the other $R_F$ radicals, Y is a trivalent or tetravalent organic linking group with from 1 to 20 carbon atoms, which can be interrupted by one or more polyvalent groups or hetero atoms selected from —O—, —S—, —N<, —NR$_1$—, —CO—, —CONR$_1$—, —NHCOO—, —CON<, —CO$_2$—, —O$_2$C—, -O$_2$CO— and —SO$_2$—, in which $R_1$ is hydrogen, $C_1$–$C_{20}$alkyl, di-$C_1$–$C_2$alkylamino-$C_2$–$C_6$alkylene, hydroxy-$C_1$–$C_5$alkylene or $C_1$–$C_5$alkyl or hydroxy-$C_1$–$C_5$alkylene which is substituted by pyridyl, piperidyl or cyclohexyl, X is OH, O—CH$_2$—COOH or COOH, a is 1 or 2, b is 2 or 3, L is O, S or NR', in which R' is $C_1$–$C_{20}$hydrocarbyl, hydroxy-$C_2$–$C_5$alkylene, carboxymethylene or U—OH,

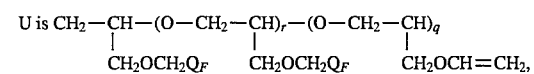

U is CH$_2$—CH—(O—CH$_2$—CH)$_r$—(O—CH$_2$—CH)$_q$
         |                |                    |
         CH$_2$OCH$_2$Q$_F$   CH$_2$OCH$_2$Q$_F$     CH$_2$OCH=CH$_2$,

Z is H or a mono-, di-, tri- or tetravalent organic group of 1–40 carbon atoms which can be interrupted by one or more polyvalent groups or hetero atoms selected from —O—, —S—, —N<, —NR$_1$—, —CO—, —CONR$_1$—, —NHCOO—, —CON<, —CO$_2$, —O$_2$C—, —O$_2$CO— and —SO$_2$—, and can also be substituted by hydroxyl, carboxyl, carboxyalkyl or sulfonate when L is S or NR', r and q are each, independently, 0 to 10, c is 1 to 4, d is 1 to 3, with the proviso that when c and d are both 1, Z is monovalent and r is >0, and e is 0 or 1, with the proviso that when e is 0, d is 2 and L is S or NR'.

The alkyl and alkylene groups encompassed by Y, Z, $R_1$ and R' can be linear, branched or carbocyclic, including phenylene. The term hydrocarbyl includes alkyl, alkenyl, aryl and alkaryl.

Preferred are compounds of the formulae I and II wherein $Q_F$ is $Q_{F2}$ and $R_F$ is saturated, contains 6–18 carbon atoms, is fully fluorinated and contains at least one terminal perfluoromethyl group. Most preferably, $R_F$ is a fully fluorinated, linear carbon chain with 6 to 14 carbon atoms.

Preferred compounds of the formula I are those wherein Y is a trivalent or tetravalent hydrocarbyl linking group with from 2 to 10 carbon atoms.

Preferred alcohols of the formula I (X=OH) of this invention are $(Q_{F2}CH_2OCH_2)_2CHOH$, $(Q_{F2}CH_2OCH_2)_2C(CH_2OH)_2$, $(Q_{F2}CH_2OCH_2)_3C-CH_2OH$ and $(Q_{F2}CH_2OCH_2)_2C(C_2H_5)CH_2OH$. The last two are especially preferred.

Typical examples of acids of the formula I (X=COOH) of this invention include

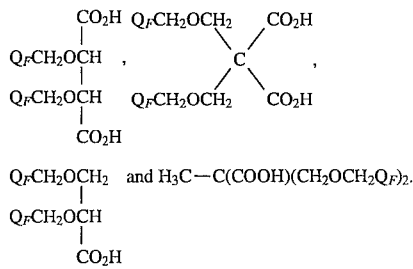

$Q_FCH_2OCH_2$ and $H_3C-C(COOH)(CH_2OCH_2Q_F)_2$.
|
$Q_FCH_2OCH$
|
$CO_2H$

Also useful are amino acids obtained by reaction of mono- or diamino acids with allyl chloride or allyl bromide, for example the compound of formula

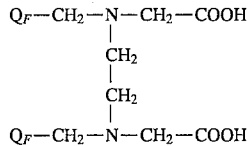

where $Q_F$ is as defined above, which is obtained by reaction of ethylenediamine diacetic acid (EDDA) with allyl chloride.

Preferred compounds of the formula II are those wherein $Q_F$ is $Q_{F2}$ and $R_F$ is saturated, contains 6–18 carbon atoms, is fully fluorinated and contains at least one terminal perfluoromethyl group, r is equal to or greater than q and the sum of r plus q is 0 to 10. Most preferably $R_F$ is a fully fluorinated, linear carbon chain with 6 to 14 carbon atoms, r is is equal to or greater than q and is 0 to 5 and q is 0 to 3.

In one preferred embodiment, L is O, c and d are 1 and Z is phenyl, carboxyphenyl, p—n—$C_1$–$C_{10}$alkylphenyl, a monovalent alkyl or alkenyl radical with 1–20 carbon atoms which may be interrupted by —O—, —S— or —$NR_1$— groups, and may be substituted by one or two carboxyl groups, or is hydroxy-$C_2$–$C_5$alkylene, such as the monoradical residue (minus 1 OH group) of ethanol, propanol, butanol, isopropanol, decanol, 10,11-undecenol, ethylene glycol, N,N-dimethylaminopropanol, p-hydroxybenzoic acid, phenol or p-octylphenol.

In another preferred embodiment, L is O, c is 2, d is 1 and Z is 1,4-phenylene or a divalent alkylene radical which may be interrupted by —O—, —S— or —$NR_1$— groups and substituted by one or two carboxyl groups. Typical examples of Z are the radical residues of glycols or polyols (minus 2 OH groups) such as those of ethylene glycol, propylene glycol, hexylene glycol, polyoxyethylene glycols, i.e. —$(CH_2CH_2O)_nCH_2CH_2$— where n is 2–20, hydroquinone, glycerol, trimethylolpropane, 2,2-bishydroxymethylpropionic acid methyl ester, N-methyldiethanolamine, triethanolamine, 3-(diethylamino)-1,2-propanediol and of alkoxylated and polyalkoxylated primary or bis-secondary amines, with —$CH_2CH_2$— and $CH_3N(CH_2CH_2-)_2$ being preferred.

In another preferred embodiment, L is O, c is 3, d is 1 and Z is a trivalent alkylene radical which may be interrupted by —O—, —S— or —$NR_1$— groups. Examples are the triradical residue of a polyol (minus 3 OH groups), such as $CH_3CH_2C(CH_2-)_3$ (from trimethylpropane) or —$CH(CH_2-)_2$ (from glycerol), and of alkoxylated and polyalkoxylated primary aminoalkanols.

In another preferred embodiment, L is O, c is 4, d is 1 and Z is a tetravalent residue of a polyol (minus 4 OH groups), such as from pentaerythritol, i.e. $C(CH_2-)_4$, N,N,N',N'-tetrakis( 2-hydroxypropyl)ethylenediamine, N,N,N'N'-tetrakis(2-hydroxyethyl)ethylenediamine or polyalkoxylated diprimary diamines.

In another preferred embodiment, L is S, d is 2 and Z is either a direct bond if e is 1 or e is 0.

In another preferred embodiment, L is S, d and c are 1 and Z is a monovalent linear or branched alkyl radical with 1–20 carbon atoms, hydroxy-$C_2$–$C_5$alkylene, carboxy-$C_2$–$C_4$alkylene or —$CH(COOH)CH_2COOH$, with —$CH_2CHOHCH_2OH$, —$CH_2CH_2COOH$ and —$CH(COOH)CH_2COOH$ being preferred.

In another preferred embodiment, L is S, d is 1, c is 2 and Z is a divalent $C_2$–$C_{20}$alkylene radical which may be interrupted by —O— or —$NR_1$—.

Alcohols of formula II of this invention also include those wherein L is NR', in which R' is U—OH, $C_1$–$C_5$alkyl or carboxymethylene, c, d and e are each 1 and Z is monovalent.

When L is NR', in which R' is U—OH, Z is preferably a monovalent alkyl radical with 1–20 carbon atoms which may be interrupted by —O—, —S— or —$NR_1$— groups or a phenyl radical, which radicals may be substituted by hydroxy, carboxy or sulfonate groups. Z is most preferably the radical residue (minus 1 $NH_2$) of butylamine, aminoethanol, 1,1-dihydroxymethylaminopropane, tris(hydroxymethyl)aminomethane, glucamine, p-aminobenzoic acid, beta-alanine or HOOC—CH($NH_2$)—A, wherein A is the radical residue of an α-amino acid such as glycine, alanine, aspartic acid, glutamic acid or murine.

In alcohols of formula II wherein L is NR' and R' is U—OH, Z as HOOC—$CH_2CH_2$—, HOOC—$CH_2$—, HOOC—$CH(CH_3)$—, —$CH_2CH_2SO_3H$, —CH(COOH)—$(CH_2)_{1-2}COOH$, —$C(C_2H_5)(CH_2OH)_2$ and $(CH_3)_2N(CH_2)_3$— are most especially prefered.

When L is NR', in which R' is $C_1$–$C_5$alkyl or carboxymethylene, Z is most preferably the radical residue (minus 1 $NHR_1$) of a secondary amine, such as diethanolamine, dibutylamine, N-methyltaurine or sarcosine.

In other embodiments, L is NR', c is 2 to 4, d is 2 and R' is U—OH, or d is 1 and R' is alkyl with 1–5 carbon atoms or a carboxymethylene group, and Z is a divalent alkylene radical with 2 to 12 carbon atoms which can be interrupted by —O—, —S— or —$NR_1$— groups and substituted by hydroxy, carboxy or sulfonate groups. Typical examples of Z are the diradical residues (minus 2 $NH_2$ or $NHR_1$ groups)

of diprimary amines, disecondary amines or primary-secondary amines, such as those of 1,3-diaminopropane, 1,3-diamino-2-hydroxypropane, 2-(2-aminoethylamino)-ethanol, N,N'-bis(2-hydroxyethyl)-ethylenediamine, ethylenediamine diacetic acid and lysine, with N,N'-bis(2-hydroxyethyl)ethylenediamine and ethylenediamine diacetic acid being preferred.

Preferred alcohols of the formula II of this invention include $(Q_{F2}CH_2OCH_2CH(OH)CH_2)_2N$—$C(CH_2OH)_2C_2H_5$, $(Q_{F2}CH_2OCH_2CH(OH)CH_2)_2S$, $(Q_{F2}CH_2OCH_2CH(OCH_2CH_2OH)CH_2)_2S$ and $Q_{F2}CH_2OCH_2CH(OH)CH(OH)CH_2OCH_2Q_{F2}$.

The alcohols and diols of this invention can be used to make a variety of products such as esters, ether-alcohols, carbonates, carboxylic acids, phosphates, sulfates and urethanes, which are other objects of this invention. Preferred are derivatives of the alcohols and diols where $Q_F$ is $Q_{F2}$.

Among the preferred esters are those of the formulae Ia and IIa $$(Q_{F2}CH_2O)_b\text{—}Y\text{—}(O_2C\text{—}R_3)_a \quad (Ia)$$

and $$Z(\text{—}L\text{—}(U\text{—}O_2C\text{—}R_3)_d)_c \quad (IIa)$$

wherein $Q_{F2}$, Y, a, b, Z, L, U, d and c are as defined above and $R_3$ is H or $C_1$–$C_{20}$hydrocarbyl, which may be substituted by one or more hydroxyl, thiol or carboxyl groups. Typical examples of —$O_2C$—$R_3$ include the radicals of acetic, benzoic, hydroxybenzoic, terephthalic, phthalic, acrylic, methacrylic, citric, maleic, fumaric, itaconic, malonic, succinic, thioacetic, thiopropionic and thiosuccinic acids. Addition polymers may be derived from the acrylates, methacrylates or fumarates.

Preferred esters of the formula Ia are acrylates, methacrylates, maleates, fumarates, succinates and ortho- and terephthalates of the alcohols of the formulae $(Q_{F2}CH_2OCH_2)_2CHOH$, $(Q_{F2}CH_2OCH_2)_2C(CH_2OH)_2$, $(Q_{F2}CH_2OCH_2)_3C$—$CH_2OH$ and $(Q_{F2}CH_2OCH_2)_2C(C_2H_5)CH_2OH$, wherein $Q_{F2}$ is as defined above.

Also preferred are acrylates, methacrylates, maleates, fumarates, succinates and ortho- and terephthalates of diols of the formulae IIb and IIc $$Z_e\text{—}N\text{—}(U\text{—}OH)_2 \quad (IIb)$$

and $$Z_e\text{—}(O\text{—}U\text{—}OH)_2 \quad (IIc),$$

wherein, in the definition of U, r is equal to or greater than q and is 0 to 5, q is 0 to 3 and, when e is 1, Z is a monovalent hydrocarbyl radical with 1–20 carbon atoms which may be interrupted by —O—, —S— or —$NR_1$— and may be substituted by hydroxy or carboxy groups, or, when e is 2, Z is 1,4-phenylene or a divalent alkylene radical which may be interrupted by —O—, —S— or —$NR_1$— groups, wherein $R_1$ is as defined above. Most preferably, Z is a monovalent alkyl radical with 1–18 carbon atoms or is —$CH_2CH_2$—.

Also useful are polyesters of the formulae Id and IId

$$\text{—}(Y\text{—}O_2C\text{—}R_4\text{—}CO_2)_n\text{—} \quad (Id)$$

and $$\text{—}(U\text{—}L\text{—}Z\text{—}L\text{—}U\text{—}O_2C\text{—}R_4\text{—}CO_2)_n\text{—}, \quad (IId)$$

wherein Y is a tetravalent organic linking group with from 2 to 20 carbon atoms, Z is a divalent alkylene radical with 2 to 12 carbon atoms which can be interrupted by —O—, —S— or 1,4-phenylene and substituted by 1 or 2 carboxyl groups, n is an integer from 2 to 100, preferably 3 to 10, $Q_{F2}$, U, and L are as defined above and $R_4$ is the divalent radical residue of a dicarboxylic acid of the formula HOOC—$R_4$—COOH.

$R_4$ is preferably a direct bond, an alkylene of 1–16 carbon atoms, an arylene of 6 to 14 carbon atoms or an alkarylene of 7 to 18 carbon atoms. Such acids include oxalic, malonic, succinic, glutaric, adipic, pimelic, suberic, azelaic, sebacic, brassylic, octadecanedioic, dimer acid, 1,4-cyclohexanedicarboxylic, 4,4'-dicyclohexyl-1,1'-dicarboxylic, phthalic, isophthalic, terephthalic, methylphthalic, diphenyl-2,2'-dicarboxylic, diphenyl-4,4'-dicarboxylic, 1,4-naphthalene dicarboxylic, diphenylmethane-2,2'-dicarboxylic, diphenylmethane-3,3'-dicarboxylic, diphenylmethane-4,4'-dicarboxylic acid and the like. Also useful are compounds wherein $R_4$ is substituted by one or two carboxy groups and is derived, for example, from pyromellitic anhydride or benzene tetracarboxylic acid dianhydride.

Especially preferred are polyesters of the formula Id wherein Y is —$CH_2(CH\text{—})CH_2$—S—$CH_2(CH\text{—})CH_2$— or —$CH_2(CH\text{—})CH_2$—NR'—$CH_2(CH\text{—})CH_2$— and $R_4$ is —CH=CH—, —$(CH_2)_{2-8}$— or 1,3- or 1,4-phenylene, and polyesters of the formula IId wherein L is O, $R_4$ is —CH=CH—, —$(CH_2)_{2-8}$— or phenylene, Z is a divalent alkylene radical which may be interrupted by —O—, —S— or —$NR_1$— groups and, in the definition of U, r is equal to or greater than q and is 0 to 5 and q is 0 to 3.

Useful phosphates are the mono- and diphosphates and bis-monophosphates of alcohols and polyols of the formulae I and II. Preferred monophosphates of alcohols and polyols of the formula I are those from alcohols and diols of the formulae $(Q_{F2}CH_2OCH_2)_2CHOH$, $(Q_{F2}CH_2OCH_2)_2C(CH_2OH)_2$, $(Q_{F2}CH_2OCH_2)_3C$—$CH_2OH$ and $(Q_{F2}CH_2OCH_2)_2C(C_2H_5)CH_2OH$, wherein $Q_{F2}$ is as defined above.

Especially preferred are phosphates of alcohols and polyols of the formula I wherein Y is —$CH_2(CH\text{—})CH_2$—S—$CH_2(CH\text{—})CH_2$— or —$CH_2(CH\text{—})CH_2$—NR'—$CH_2(CH\text{—})CH_2$— as well as phosphates of the formula

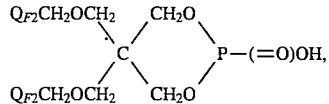

wherein $Q_{F2}$ is as defined above.

Also preferred are monophosphates of diols of the formula II wherein, in the definition of U, r is equal to or greater than q and is 0 to 5 and q is 0 to 3.

Also preferred are monophosphates of diols of the formula II wherein U is as defined above, L is O and Z is phenyl, p—n—$C_1$–$C_{10}$alkylphenyl, a monovalent alkyl radical with 1–20 carbon atoms which may be interrupted by —O—, —S— or —$NR_1$— groups, or is hydroxy-$C_2$–$C_5$alkylene.

Also preferred are monophosphates of diols of the formula II wherein U is as defined above, L is O and Z is 1,4-phenylene or a divalent alkylene radical which may be interrupted by —O—, —S— or —$NR_1$— groups.

Also preferred are monophosphates of diols of the formula II wherein U is as defined above, L is O and Z is a trivalent alkylene radical which may be interrupted by —O—, —S— or —NR$_1$—.

Also preferred are monophosphates of diols of the formula II wherein U is as defined above, L is S and Z is a direct bond or a divalent C$_2$–C$_{20}$alkylene radical which may be interrupted by —O— or —NR$_1$—.

Also preferred are monophosphates of diols of the formula II wherein U is as defined above, L is NR', wherein R' is U—OH and Z is a divalent alkylene radical with 2 to 12 carbon atoms which can be interrupted by —O—, —S— or —NR$_1$— groups and substituted by hydroxy or carboxy groups.

Most preferred are monophosphates of diols of the formula II wherein U is as defined above, L is O and Z is —CH$_2$CH$_2$— or CH$_3$CH$_2$C(CH$_2$—)$_3$, and phosphates of the formula

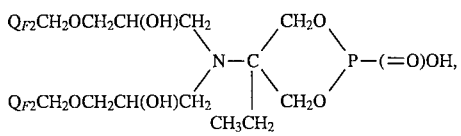

wherein Q$_{F2}$ is as defined above.

Useful sulfates are the mono- and disulfates of alcohols and polyols of the formulae I and II. Preferred monosulfates of alcohols and polyols of the formula I are those from alcohols and diols of the formulae (Q$_{F2}$CH$_2$OCH$_2$)$_2$CHOH, (Q$_{F2}$CH$_2$OCH$_2$)$_2$C(CH$_2$OH)$_2$, (Q$_{F2}$CH$_2$OCH$_2$)$_3$C—CH$_2$OH and (Q$_{F2}$CH$_2$OCH$_2$)$_2$C(C$_2$H$_5$)CH$_2$OH, wherein Q$_{F2}$ is as defined above.

Also preferred are monosulfates of diols of the formula II wherein, in the definition of U, r is equal to or greater than q and is 0 to 5 and q is 0 to 3.

Also preferred are monosulfates of diols and polyols of the formula II wherein U is as defined above, L is O and Z is phenyl, p—n—C$_1$–C$_{10}$alkylphenyl, a monovalent alkyl radical with 1–20 carbon atoms which may be interrupted by —O—,—S— or —NR$_1$— groups, or is hydroxy-C$_2$–C$_5$alkylene.

Also preferred are monosulfates of diols and polyols of the formula II wherein U is as defined above, L is O and Z is 1,4-phenylene or a divalent alkylene radical which may be interrupted by —O—, —S— or —NR$_1$— groups.

Also preferred are monosulfates of diols and polyols of the formula II wherein U is as defined above, L is O and Z is a trivalent alkylene radical which may be interrupted by —O—, —S— or —NR$_1$— groups.

Also preferred are monosulfates of diols and polyols of the formula II wherein U is as defined above, L is S and Z is a direct bond or a divalent C$_2$–C$_{20}$alkylene radical which may be interrupted by —O— or —NR$_1$—.

Also preferred are monosulfates of diols and polyols of the formula II wherein U is as defined above, L is NR', R' is U—OH and Z is a monovalent alkyl radical with 1 to 20 carbon atoms which be interrupted by —O—, —S— or —NR$_1$— groups and substituted by hydroxy or carboxy groups.

The most preferred monosulfates of diols of the formula II are those wherein U is as defined above, L is O and Z is —CH$_2$CH$_2$—, and those of the formulae CH$_3$CH$_2$—C—(CH$_2$OCH$_2$CH(OH)CH$_2$OCH$_2$Q$_{F2}$)$_3$ and (HOCH$_2$)$_2$(C$_2$H$_5$)—C—N(CH$_2$OCH$_2$CH(OH)CH$_2$OCH$_2$Q$_{F2}$)$_2$.

Useful polyurethanes consist of or contain units of the formulae Ie or IIe

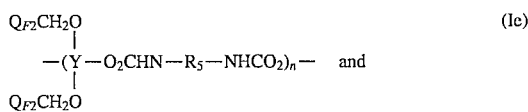

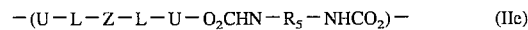

wherein Y, U and L are as defined as above, Z is a divalent radical as defined above and R$_5$ is the diradical residue of a diisocyanate of the formula OCN—R$_5$—NCO.

Useful aromatic diisocyanates of the formula OCN—R$_5$—NCO include toluene diisocyanate (TDI) (all isomers), 4,4'-diphenylmethane diisocyanate (MDI), tolidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl- 4,4'-bisphenylene diisocyanate, 4,4'-bis(2-methylisocyanatophenyl)methane, 4,4'-bisphenylene diisocyanate, 4,4'-bis(2-methoxyisocyanatophenyl)methane, 1-nitrophenyl- 3,5-diisocyanate, 4,4'-diisocyanatodiphenyl ether, 3,3'-dichloro-4,4'-diisocyanatodiphenyl ether, 3,3'-dichloro-4,4'-diisocyanatodiphenyl methane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3'-dichloro-4,4'-diisocyanatodiphenyl, 1,2-naphthalene diisocyanate, 4-chloro-1,2-naphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate and 7-methyl-1,3-naphthalene diisocyanate.

Useful aliphatic or cycloaliphatic polyisocyanates include 1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,8-octane diisocyanate, 1,10-decane diisocyanate, 1,12-dodecane diisocyanate, 1,16-hexadecane diisocyanate and other aliphatic diisocyanates such as 1,3- and 1,4-cyclohexane diisocyanate.

Additionally, the following diisocyanates are particularly preferred because urethane compositions made therefrom tend to be non-yellowing: 1,6-hexamethylene diisocyanate (HDI), 2,2,4- and 2,4,4-trimethylhexamethylene diisocyanate (TMDI), dimer acid derived diisocyanate (DDI) obtained from dimerized fatty acids such as linoleic acid, 4,4'-dicyclohexylmethane diisocyanate (hydrogenated MDI), isophorone diisocyanate, 3-isocyanatomethyl-3,5,5-trimethylcyclohexyl diisocyanate, lysine methyl ester diisocyanate (LDIM), bis(2-isocyanatoethyl) fumarate (FDI), bis(2-isocyanatoethyl) carbonate and m-tetramethylxylylene diisocyanate (TMXDI).

Preferred are polyurethanes of 3,000 to 30,000 molecular weight of the formula Ie and containing repeating units of the formulae

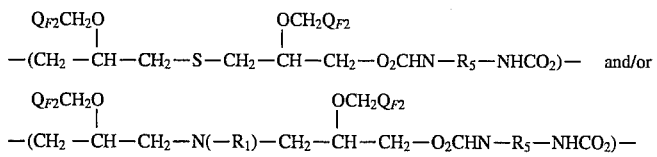

$$-(CH_2-CH-CH_2-S-CH_2-CH-CH_2-O_2CHN-R_5-NHCO_2)- \quad \text{and/or}$$

with $Q_{F2}CH_2O$ above the third carbon and $OCH_2Q_{F2}$ above the sixth carbon.

$$-(CH_2-CH-CH_2-N(-R_1)-CH_2-CH-CH_2-O_2CHN-R_5-NHCO_2)-$$

with $Q_{F2}CH_2O$ above the third carbon and $OCH_2Q_{F2}$ above the sixth carbon.

wherein $R_1$ is $C_1$–$C_5$ alkyl, $R_5$ is is the diradical residue of isophorone diisocyanate, 2,2,4-(2,4,4)-trimethylhexamethylene diisocyanate or 1,6-hexamethylene diisocyanate and $Q_{F2}$ is as defined above.

Also preferred are polyurethanes of 3,000 to 30,000 molecular weight and containing repeating units of the formula IIe wherein, in the definition of U, r is equal to or greater than q and is 0 to 5, q id 0 to 3, U is as defined above, L is O, Z is —$CH_2CH_2$— and $R_5$ is the diradical residue of isophorone diisocyanate, 2,2,4-(2,4,4)-trimethylhexamethylene diisocyanate or 1,6-hexamethylene diisocyanate.

Also preferred are polyurethanes of 3,000 to 30,000 molecular weight and containing units of the formula IIe wherein U is as defined above, L is S and Z is a direct bond.

Also especially preferred are polyurethanes of 3,000 to 30,000 molecular weight and containing units of the formula IIe wherein U is as defined above, L is NR', wherein R' is $C_1$–$C_5$alkyl and Z is a divalent $C_2$–$C_{12}$alkylene radical.

Also especially preferred are polyurethanes of 3,000 to 30,000 molecular weight and containing units of the formula IIe wherein U is as defined above, L is NR', wherein R' is U—OH and Z is a monovalent radical with 1 to 20 carbon atoms which be interrupted by —O—, —S— or —$NR_1$— groups.

It is within the scope of this invention to further react these polyurethanes with diisocyanates and polyisocyanates, or to incorporate the novel $R_F$-diols into polyurethane resin systems to make crosslinked polyurethanes, such as coatings or foams, as is known to those skilled in the art of polyurethane chemistry.

Ether derivatives of the formula If are also useful $$(Q_{F2}CH_2O)_b—Y—(O—CH_2CH(OH)R_6)_a \quad \text{(If)}$$

wherein $R_6$ is hydrogen, a hydrocarbon radical with 2 to 20 carbon atoms, or a polyethylene oxide radical —$(OCH_2CH_2)_u$—$R_7$, wherein $R_7$ is OH or $(Q_{F2}CH_2)_b$—Y—O—$CH_2CH(OH)$, u is an integer from 2 to 50 and $Q_{F2}$, Y, a and b are as defined above.

Especially useful are ether acids of the formula I wherein X is O—$CH_2$—COOH and Q is $Q_{F2}$, wherein $Q_{F2}$, Y, a and b are as defined above.

It is understood that an $R_F$ group usually represents a mixture of perfluoroalkyl moieties. When the $R_F$ group is identified as having a certain number of carbon atoms, said $R_F$ group also usually concomitantly contains a small fraction of perfluoroalkyl groups with fewer carbon atoms and a small fraction of perfluoroalkyl groups with more carbon atoms. Commonly the perfluoroalkyl moiety is a mixture of $C_4F_9$, $C_6F_{13}$, $C_8F_{17}$, $C_{10}F_{21}$, $C_{12}F_{25}$, and $C_{14}F_{29}$ groups.

The novel $R_F$-alcohols of this invention are obtained by the reaction of a perfluoroalkyl iodide with an allyloxy alcohol, to first yield an iodide compound wherein $Q_F=QF_1$, followed by dehydrohalogenation of the iodide with a base to yield an unsaturated alcohol with $Q_F=Q_{F2}$. Useful commercial allyloxy alcohols are pentaerythritol di- and triallyl ether and trimethylolpropane diallyl ether. Other alcohols can be synthesized as follows: polyallyl ethers by reaction of triols, tetraols and of polyols in general with allyl glycidyl ether; glycerol-1,3-diallyl ether by reaction of equimolar amounts of allyl alcohol and allyl glycidyl ether; diallyl alcohols or diols by reaction of allyl chloroformate with diamino alcohols or diols; thioether or tertiary amino group-containing diallyldiols by reaction of two moles of allyl glycidyl ether with one mole of sodium sulfide or an organic dithiol, or with a primary or di-secondary amine, as is shown in the Examples.

Similarly, the novel $R_F$-acids can be prepared by the reaction of a perfluoroalkyl iodide and an allyloxy acid or its ester, to yield an iodide compound, followed by dehydrohalogenation with a base and, if the product is an ester, hydrolysis to the free acid. Useful allyloxy acids can be prepared advantageously from allyl glycidyl ether and mono- or diaminoacids, mercaptoacids and hydroxyacids, or from allyl chloride or bromide by reaction with ester-alcohols, followed by hydrolysis of the ester group. Also useful is the diallyl-diacid obtained by reaction of allyl chloride or allyl bromide with ethylenediamine diacetic acid.

Compounds of the formula II can be obtained by the reaction of 2–20 moles of allyl glycidyl ether with a compound having 1–4 active hydrogens such as an alcohol, diol, triol, tetraol or a compound of the formula Z(—OH)$_{1-4}$; a thiol, dithiol or a compound of the formula Z(—SH)$_{1-2}$; a secondary amine, disecondary amine or a compound of the formula Z(—NR$_1$)$_{1-2}$, where Z in each case is as defined above, which product is then further reacted with 2–20 moles of a perfluoroalkyl iodide in the presence of a free radical initiator to gave an $R_F$I- adduct which is then dehydroiodinated with a base.

Suitable alcohols for preparing compounds of the formula II are those with 1 to 20 carbon atoms such as methanol, isopropanol, allyl alcohol, 11-undecenol, N,N-dimethylaminoethanol and hydroxybenzoic acid, alkoxylated $C_1$–$C_{20}$alkanols such as $C_{18}H_{37}(OCH_2CH_2)_{5-50}OH$ and alkoxylated $C_1$–$C_{10}$alkylphenols such as $C_9H_{19}C_6H_4(OCH_2CH_2)_5$—OH. Useful diols include alkylene glycols with 2–6 carbon atoms such as ethylene or propylene glycol, 2,2-bishydroxymethylpropionic acid methyl ester hydroxypropionic acid, N-methyl diethanolamine, allyl glycerol and polypropylene oxide- or polybutylene oxide-derived diols with 2–20 repeating units. Useful triols include trimethylolpropane, glycerine and butanetriol. Useful tetraols include pentaerythritol and erythritol. Useful thiols include mercaptopropionic acid, thioglycerol, thiophenol and ethylene dimercaptopropionate. Useful amines include butylamine, N,N-dimethylpropane-1,3-diamine, alanine, glutamic acid, aspartic acid and 1,1-dihydroxymethylpropylamine.

The addition and/or oligomerization of allyl glycidyl ether can be carried out under anhydrous conditions using a base such as sodium hydroxide or an acidic catalyst such as $BF_3$. Addition reactions of allyl glycidyl ether with amines or thiols can be carried out in an aqueous medium using base catalysis.

The addition of an $R_F$-iodide to an allyl alcohol or acid proceeds readily in the presence of a free radical initiator such as an azo compound or peroxide at conventional initiation temperatures of 35° to 150° C. It was found, however, that only in the presence of small amounts of aqueous solutions of sulfite, bisulfite or dithionate ions does the reaction proceed fast enough and are conversions high enough to make the synthesis commercially practical. The novel process to make the compounds of this invention is described separately in copending application Ser. No. 08/270,068 filed Jul. 1, 1994.

Solvents can be present during the $R_F$-iodide addition reaction; for example ketones such as acetone, methyl ethyl ketone or methyl propyl ketone, esters such as isopropyl acetate, alcohols such as ethanol or butanol, ethers such as dioxane or di(2-hydroxyethyl) ether, hydrocarbons such as toluene or octane, amides such as dimethylformamide and lactams such as N-methylpyrrolidone.

The dehydrohalogenation of the $R_F$-iodide addition product is generally carried out in water at 50° to 100° C. by reacting the adduct with a strong inorganic base, such as sodium or potassium hydroxide or a strong organic base such as 1,8-diazabicyclo(5.4.0)-undec- 7-ene (DBU) over a period of several hours. The product is obtained in the non-aqueous phase. The solvent can be stripped off and the product be washed with water and isolated as a solid by filtration, or it can be discharged from the reactor as a melt; alternatively, it can be isolated as a solution by allowing a clean phase separation to occur between the aqueous and organic phases. The mode of isolation will depend on the specific product. The product is analyzed for its hydroxyl value prior to further reaction. Trans-olefins are formed predominately, with the cis-/trans ratio being determined by NMR.

The alcohols of the formulae I and II can be further reacted with phosphorous pentoxide, $POCl_3$ or polyphosphoric acid to make phosphate ester-acids, or with chlorosulfonic acid or sulfamic acid to make sulfate ester-acids which are useful as paper sizes. By reacting alcohols of the formula I or II with chloroacetic acid, bromoacetic acid or the like, carboxylic acids can be prepared for use as paper sizes. The alcohols and diols can also be reacted with dicarboxylic acids, dicarboxylic acid anhydrides, tetracarboxylic acid dianhydrides or with diacid chlorides to prepare carboxylic ester-acids. By reaction with phosgene, dimethylcarbonate or ethylene bischloroformate, carbonates and polycarbonates can be prepared.

The novel di- and poly-$R_F$-acids of this invention—for example compounds of the formula I wherein X is O—$CH_2$—COOH or COOH; compounds obtainable by reacting alcohols of the formulae I and II with dicarboxylic acids, dicarboxylic acid anhydrides, tetracarboxylic acid dianhydrides or with diacid chlorides; sulfates, sulfonates and phosphates of alcohols of the formulae I and II and compounds of the formula II wherein Z is substituted by carboxyl, carboxyalkyl or sulfonate and their salts—are useful as paper sizes which impart outstanding oil and water repellency. The excellent oil repellancy obtained with these novel compounds is attributed to their bis-$R_F$-structure. As a notable exception, however, it was found that 11-perfluoroalkyl-10-undecenoic acid, $R_F$—CH=CH—$(CH_2)_8$—COOH, and 11-perfluoroalkyl-10-undecenyl sulfate, in salt form, perform excellently as an internal paper sizes, perhaps due to their long, linear 2-phase structure. Useful salts are alkali metal, ammonium and amine salts, with ammonium, and mono-. di- and tri-$C_1$-$C_5$alkyl and mono-, di- and tri-$C_1$-$C_5$hydroxyalkyl ammonium salts being preferred. Typical salts are those of diethanolamine.

The use of 11-perfluoroalkyl-10-undecenoic acid and of 11-perfluoroalkyl-10-undecenyl sulfate as internal oil repellent paper sizes is another object of this invention.

Polyurethanes are prepared from the $R_F$-diols of this invention by the known methods of polyurethane chemistry. These polyurethanes may contain other building blocks derived from diols or diamines, especially tertiary amino group-containing diols such as N-methyldiethanolamine, poly(ethylene oxide)diols and 3-aminopropyl-terminated poly(ethylene oxide) (Jeffamine-ED, from TEXACO Corp.), poly(dimethylsiloxane)dialkanols and poly(dimethylsiloxane)diaminoalkyls. Typical polyurethane compositions incorporating these and other diols and diamines in combination with certain other perfluoroalkyl-substituted diols are described for example in U.S. Pat. Nos. 3,968,066, 4,046, 944 and 4,098,742. Polyurethanes prepared from the $R_F$-diols of this invention are useful as as oil- and water-repellant coatings on textiles, paper, wood and other substrates.

Preferably a sufficient amount of an organofluorine compound of this invention is employed to provide 0.01 to 1%, especially 0.03 to 0.2% F to a substrate.

EXPERIMENTAL PART

The following examples illustrate various embodiments of the invention, and are not to be interpreted as limiting the scope of the appended claims. In the examples all parts are by weight unless otherwise specified.

Example 1

1-Butanol,
2,2-bis(((4,4,5,5,6,6,7,7,8,8,9,9,10,10,11,11,11-heptadecafluoro-2-undecenyl)oxy)methyl)-

Into a three neck 250 ml round-bottomed flask are placed 22.7 g (0.042 mol) of 1-iodoperfluorooctane, 4.3 g (0.02 mol) of trimethylolpropane diallyl ether (NEOALLYL T-20; 86% by weight diallyl-, 8% monoallyl-, 8% triallyl-substituted, from DAISO Co., Ltd). and 10 g of deionized water. This mixture is placed under nitrogen and heated to 75° C. To the two phase reaction mixture are added 0.22 g (1.37 mmol) of 2,2-azo-bis-isobutyronitrile (AIBN) and 0.2 g (0.002 mol) of sodium bisulfite. After 8 hours the reaction is complete as determined by gas chromatography and the aqueous phase is separated. The reaction mixture is washed twice with 40 g of deionized water at 75° C. Dehydrohalogenation is performed by the addition of 40 g of deionized water and 7.6 g (0.05 mol) of 1,8-diazabicyclo(5.4.0)undec-7-ene (DBU). This mixture is stirred at 80° C. for 5 hours. The aqueous layer is removed and the reaction mixture is washed with 40 g of deionized water, followed by 40 g of 5% HCl and finally with another 40 g of deionized water. The title product is isolated as a tan oil in a yield of 19.4 g(72%). MS, m/z (M+); calculated, 1050.0870; observed, 1050.0842. $^1$H-NMR (500 MHz, $CDCl_3$) d6.44(dm, 2H, —$CF_2CH$=CH—, J=15.3Hz), 5.89(dt, 2H, —$CF_2CH$=CH—, J=15.3Hz and J=11.9Hz), 4.14(bs, 4H, —$CF_2CH$=$CH_2$—), 3.63(s, 2H, —$CH_2OH$), 3.52(d, 2H, $OCH_aH_bC$—, $J_{a,b}$= 9.2Hz), 3.49(d, 2H, —$OCH_aH_bC$—, $J_{a,b}$=9.2Hz), 1.42(q, 2H, —$CH_2CH_3$, J=7.7Hz) and 0.88(t, 3H, —$CH_2CH_3$, J=7.7Hz). The product contains 93% of the trans isomer as determined from integration of the $^1$H-NMR spectrum.

Example 2

1-Propanol,
3-((4,4,5,5,6,6,7,7,8,8,9,9,10,10,11,11,11-heptadecafluoro-
2-undecenyl)oxy)-2,2-bis(((4,4,5,5,6,6,7,7,8,8,9,9,
10,10, 11,11,11-heptadecafluoro-
2-undecenyl)oxy)methyl)

Into a 100 ml three neck round-bottomed flask are placed 0.64 g (2.5 mmol) of the triallyl ether of pentaerythritol (NEOALLYL T-30, containing 15 weight % diallyl, 75% triallyl and 10% tetraallyl esters; DAISO Co., Ltd)., 5.0 g (9.2 mmol) of 1-iodoperfluorooctane and 5.0 g of deionized water. The reaction mixture is placed under nitrogen and heated to 80° C. To the stirred reaction mixture are added 0.05 g (0.30 mmol) of AIBN and 0.05 g (0.05 mmol) of sodium bisulfite. After 10 hours the reaction is complete as determined by gas chromatography. The top water layer is removed and the reaction mixture is washed twice with 5.0 g of deionized water. Dehydrohalogenation is performed by adding 2.0 g of deionized water along with 2.1 g (14.0 mmol) of DBU. This mixture is stirred under nitrogen at 80° C. for one hour, after which time the reaction is complete. The top aqueous layer is removed and the reaction mixture is washed with 2.0 g of deionized water, followed by 2.0 g of 5% HCl and finally with another 2.0 g of deionized water. The title product is isolated as a light brown oil in a yield of 2.1 g (57%). $^1$H-NMR (300 MHz, CDCl$_3$) d6.43(d, 3H, —CF$_2$CH=CH—, J=15.5Hz), 5.88(dt, 3H, —CF$_2$CH$_a$=CH$_b$CH$_2$c—, J$_{a,b}$=15.0Hz and J$_{a,c}$=7.5Hz), 4.13(bs, 6H, —CF$_2$CH=CH$_2$O—), 3.74 (s, 2H, —CH$_2$OH) and 3.55 (s, 6H, —OCH$_2$C—). The product contains 90% of the trans isomer as determined from integration of the $^1$H-NMR spectrum. MS, m/z (M$^+$); calculated, 1511.0704; found, 1511.1586.

Example 3

1-Butanol, 2,2-bis(((perfluoroC$_{6-18}$alkyl-2-propenyl)oxy)methyl)—is prepared from a perfluoroalkyl iodide (TEL-AN, from DuPont) having the following homologue distribution: 1.7% C$_6$, 49.8% C$_8$, 33.5% C$_{10}$, 11.1% C$_{12}$, 3.1% C$_{14}$, 0.69% C$_{16}$ and 0.16% and 0.16% C$_{18}$.

Into a 1000 ml round-bottomed flask are placed 277 g (0.46 mol) perfluoroalkyl iodide, 50 g (0.23 mol) trimethylolpropane diallyl ether (NEOALLYL T-20; 86% by weight diallyl-, 8% monoallyl-, 8% triallyl-substituted, from DAISO Co., Ltd.), 157 g deionized water and 55.2 g (0.69 mol) of 50% sodium hydroxide. The reaction mixture is heated to 85° C. and 1.3 g (0.007 mol) of azo-bis-isobutyronitrile (AIBN) and 0.02 mol) sodium bisulfite are added. This mixture is stirred vigorously under nitrogen. After 24 hours the reaction is complete. The top aqueous layer is removed and the reaction mixture is washed with 100 g of deionized water followed by 100 g of 5% HCl and finally with another 100 g of deionized water. The product contains 73% of the trans isomer as determined from integration of the $^1$H-NMR spectrum. The $^1$H-NMR of the trans isomer is consistent with that obtained from 1-butanol,2,2-bis(((4,4,5,5,6,6,7,7,8,8,9,9,10,10,11,11,11 -heptadecafluoro-2-undecenyl)oxy)methyl)-, of example 1. $^1$H-NMR, cis isomer: (500 MHz, CDCl$_3$) d6.23(dm, 2H, —CF$_2$CH=CH—, J=13.5Hz), 5.58(dt, 2H, —CF$_2$CH=CH—, J=15.6Hz and J=13.5Hz), 4.27(bs, 4H, —CF$_2$ CH=CH$_2$O—), 3.60(s, 2H, —CH$_2$OH), 3.48–3.42 (4H, —OCH$_a$H$_b$C— and —OCH$_a$H$_b$C—), 1.42 (q, 2H, —CH$_2$CH$_3$, J= 7.0 Hz) and 0.85 (t, 3H, —CH$_2$CH$_3$, J=7.0Hz).

Example 4

1-Propanol, 3-(perfluoroC$_{6-18}$alkyl-2-propenyl)oxy)-2,2-bis-((perfluoroC$_{6-18}$-alkyl-2 -propenyl)oxy)methyl)-, is prepared from a perfluoroalkyl iodide (TEL-AN, from DuPont) having the following homologue distribution: 1.7% C$_6$, 49.8% C$_8$, 33.5% C$_{10}$, 11.1% C$_{12}$, 3.1% C$_{14}$, 0.69% C$_{16}$ and 0.16% C$_{18}$.

Into a 2000 ml glass reactor are charged 1394 g (2.32 mol) perfluoroalkyl iodide, 200 g (0.78 mol) of triallyl ether of pentaerytrerythritol (NEOALLYL T-30, containing 15 weight % diallyl, 75% triallyl and 10% tetraallyl esters; DAISO Co., Ltd.), 2.7 g (0.014 mol) azo-bis-isobutyronitrile (AIBN) and 1.2 g (0.116 mol) sodium bisulfite, 538 g deionized water and 311 g (3.89 mol) 50% NaOH. The temperature of the mixture is increased to 85° C. and it is stirred vigorously. After 6 hours a second charge of 1.8 g (0.009 mol) of AIBN is made. After 18 hours the reaction is complete and the top aqueous layer is removed. The reaction mixture is washed with 269 g deionized water at 85° C., followed by a wash with 107.6 g of 5% HCl and a final wash with 269 g deionized water at 85° C. The product is isolated as a waxy yellow to white solid in a yield of 1249 g (95%), m.p. 72°–80° C. The product contains 73% of the trans isomer as determined from integration of the $^1$H-NMR spectrum. The $^1$H-NMR of the trans isomer is consistent with that obtained from 1-propanol, 3-((4,4,5,5,6,6,7,7,8,8, 9,9,10,10, 11,11,11-heptadecafluoro- 2-undecenyl)oxy)-2,2-bis(((4,4,5,5,6,6,7,7,8,8,9,9,10,10,11,11,11-heptadecafluoro- 2-undecenyl)oxy)methyl)-, of example 2. $^1$H-NMR, cis isomer (500 MHz, CDCl$_3$) d6.22(bm, 3H, —CF$_2$CH=CH—), 5.62 (dt, 3H, —CF$_2$CH$_a$=CH$_b$CH$_2$c—, J$_{a,b}$=13.7Hz and J$_{a,c}$= 15.4Hz), 4.28(bs, 6H, —CF$_2$CH=CH$_2$O—), 3.72 (s, 2H, —CH$_2$OH) and 3.53 (s, 6H, —OCH$_2$C—).

Example 5

1-Propyldihydrogenphosphate, 3-(perfluoro-C$_{6-18}$alkyl-2-propenyl)oxy)-2,2 -bis-((perfluoro-C$_{6-18}$alkyl-2-propenyl)oxy)methyl)-

Into a 500 ml three neck round-bottomed flask are placed 100 g (0.061 mol) of 1-propanol, 3-(perfluoro-C$_{6-18}$alkyl-2-propenyl)oxy)-2,2-bis((perfluoro-C$_{6-18}$alkyl-2 -propenyl)(oxy)methyl)-, as prepared in Example 4, along with 144 g of glyme. The temperature of this solution is increased to reflux (85° C.) and 28 g of glyme is removed by distillation. To this stirred solution is added 35.8 g (0.12 mol) of polyphosphoric acid under nitrogen. This mixture is stirred vigorously for 12 hours. After 12 hours the reaction mixture is poured into 1000 g of deionized water and a tan colored precipitate is formed. The precipitate is isolated on a Buchner funnel to give 103 g (98% yield) of the title compound, m.p. 50°–58° C.

A CDCl$_3$ solution of the product is acidified with TFA-d7 and derivatized with BSTFA. The $^{31}$P-NMR (500 MHz, CDCl$_3$), complex signals at d-18 ppm are consistent with the bistrimethylsilyl ester of 1-propyldihydrogenphosphate, 3-(perfluoro-C$_{6-18}$alkyl)oxy)- 2,2-bis((perfluoro-C$_{6-19}$alkyl)oxy)methyl)-, being the major product. Other signals at −26.4 ppm and −32 ppm are consistent with inorganic phosphorous and pyrophosphate type phosphorous respectively. Signals at −22.6 ppm and −31.3 ppm are consistent with a dimer type structure.

Example 6

2-Propanol, 1,3-bis((perfluoro-C$_{6-18}$alkyl-2-propenyl)oxy)-, is prepared using the following homologue distribution of perfluoroalkyl iodide: 1.7% C$_6$, 49.8% C$_8$, 33.5% C$_{10}$, 11.1% C$_{12}$, 3.1% C$_{14}$, 0.69% C$_{16}$ and 0.16% C$_{18}$ (TEL-AN, from DuPont).

Into a 1000 ml three neck round-bottomed flask are placed 53.0 g (0.31 mol) 1,3-diallyl ether of glycerol, 373 g (0.62 mol) perfluoroalkyl iodide, 21 g deionized water and 74.4 g (0.93 mol) 50% sodium hydroxide. The reaction mixture is placed under nitrogen and the temperature is increased to 85° C. with stirring. 1.79 g (0.93 mmol) azo-bis-isobutyronitrile are added. After 12 hours the reaction is complete. The reaction mixture is washed with 300 g deionized water at 85° C., followed by a wash with 150 g of 5% HCl and a final wash with 300 g deionized water at 85° C. The product is isolated as a waxy brown solid in a yield of 283 g (82%), m.p. 37°–45° C. The product contains 64% of the trans isomer as determined from integration of the $^1$H-NMR spectrum. $^1$H-NMR, trans isomer (500 MHz, CDCl$_3$) d6.45 (dm, 2H, —CF$_2$CH=CH—, J=14.6), 5.93 (dt, 2H, —CF$_2$CH$_a$=CH$_b$CH$_2$c—, J$_{a,b}$=14.6Hz and J$_{a,c}$=11.0Hz), 4.19(bs, 4H, —CH=CHCH$_2$O—), 4.02 (quintet, 1H, (—CH$_2$)$_2$CHOH, J=5.2Hz), 3.58 (m, 4H, (—CH$_2$$_2$CHOH). Addition of trichloroacetyl isocyanate resulted in a downfield shift of the methene proton from 4.02 to 5.23ppm. $^1$H-NMR, cis isomer (500 MHz, CDCl$_3$) d6.27(dm, 2H, —CF$_2$CH=CH—, J=12.8), 5.62 (dt, 2H, —CF$_2$CH$_a$=CH$_b$CH$_2$c—, J$_{a,b}$=12.8Hz and J$_{a,c}$=14.6Hz), 4.34 (bs, 4H, —CH=CHCH$_2$O—), 3.99 (quintet, 1H, (—CH$_2$)$_2$CHOH, J=5.2Hz), 3.58 (m, 4H, (—CH$_2$)$_2$CHOH).

Example 7

2-Propyldihydrogenphosphate, 1,3-bis((perfluoro-C$_{6-18}$alkyl-2-propenyl)oxy)-

Into a 1000 ml three neck round-bottomed flask are placed 100 g (0.089 mol) of 2-propanol, 1,3-bis((perfluoro-C$_{6-18}$alkyl-2-propenyl)oxy)-, along with 150 g of glyme. The temperature of this solution is increased to reflux (85° C.) and 15 g glyme is removed by distillation. Removal of glyme is used as a drying procedure. To this refluxing solution is added 107.3 g (0.36 mol) of polyphosphoric acid under nitrogen. This mixture is stirred vigorously for 18 hours. After 18 hours the reaction mixture is poured into 1000 g of deionized water with stirring and a brown colored precipitate forms. The precipitate is isolated on a Buchner funnel and dried under vacuum to give 94 g (88% yield), m.p. 60°–65° C.

A CDCl$_3$ solution of the product is acidified with TFA-d7 and derivatized with BSTFA. $^{31}$P-NMR (500 MHz, CDCl$_3$), shows a set of two doublets at –17.95 with J= 9Hz. These signals are consistent with the bistrimethylsilyl ester of cis/trans 2-propanol, 1,3-bis((perfluoroC$_{6-18}$alkyl-2-propenyl)oxy)-.

Example 8

Reaction of 1-Propanol, 3-((perfluoroC$_{6-18}$alkyl-2-propenyl)oxy)- 2,2-bis((perfluoroC$_{6-18}$alkyl-2-propenyl)oxy)methyl)-, with hexamethylene diisocyanate Into a flame dried 100 ml three neck round-bottomed flask are placed 20.0 g (0.012 mol) of 1-propanol, 3-(perfluoroC$_{6-18}$alkyl)oxy)-2,2-bis((perfluoroC$_{6-18}$alkyl)oxy)methyl)- along with 42 g isopropyl acetate. This solution is heated to reflux (85° C.) with stirring and 8 g isopropyl acetate is removed by distillation. To this solution is added 20 mg (0.07 m mol) of stannous octoate and 1.0 g (0.006 mol) of hexamethylene diisocyanate (HMDI). The reaction mixture turns white immediately after the addition of HMDI. Progress of the reaction is monitored by following the disappearance of the isocyanate functionality in the infrared spectrum. Isopropyl acetate is removed under vacuum to give a brown solid in a yield of 16.8 g (80%). An IR spectrum of a thin film shows an n$_{max}$ at 1715.9 cm$^{-1}$ (—O—C(O)NH—).

Example 9

Poly-(((3-perfluoroalkyl-2-propenyl)oxy)methyl)-oxirane)

A) Synthesis of
HO—(—CH$_2$CH(—CH$_2$—O—CH$_2$CH=CH$_2$)$_n$)—OH

Into a 1000 ml three neck flask equipped with a condenser, stirring shaft, thermometer and dropping funnel fitted with a gas inlet tube are added 62.1 g (1.0 mol) ethylene glycol and 2.3 g boron trifluoride etherate. 399.6 g (3.5 mol) allyl glycidyl ether is charged to the dropping funnel and dripped into the reaction vessel while stirring and introducing a stream of nitrogen gas over a period of 6 hours. The rate of addition is controlled to maintain the exotherm temperature between 70° and 80° C. After the addition is complete, the reaction mixture is heated at 80° C. for 3.5 hours. At that time a small sample is removed and analyzed using a VG Auto Spec Q hybrid mass spectrometer with Liquid SIMS technique.

The analysis shows that the oligomeric product has a chain length distribution as shown (n = number of repeat units):

| n | 1 | 2 | 3 | 4 | 5 | 6 | 7 | 8 | 9 | 10 |
|---|---|---|---|---|---|---|---|---|---|---|
| % by weight | 5.0 | 7.7 | 18.6 | 22.6 | 21.5 | 14.2 | 7.2 | 2.0 | 0.9 | 0.2 |

B) Synthesis of
HO—(—CH$_2$CH(—CH$_2$—O—CH$_2$CH=CH$_2$—R$_F$)O$_n$)—OH

To a one-liter 3-neck flask equipped with a condenser, stirring shaft and gas inlet are charged 55.2 g (0.12 mol) of the above allylether-substituted oligooxyethylene mixture, (250.0 g, 0.42 mol) perfluoroalkyl iodide with a homologue distribution of 1.7% C$_6$, 49.8% C$_8$, 33.5% C$_{10}$, 11.1% C$_{12}$, 3.1% C$_{14}$, 0.69% C$_{16}$ and 0.16% C$_{18}$ (TEL-AN, from DuPont), 125.0 g water, 2.0 g 2,2'-azo-bis-(2-methylbutyronitrile) and 0.6 g (0.006 mol) sodium bisulfite. The resultant reaction mixture is heated to 80° C. and held at this temperature for 6 hours with stirring and introducing a stream of nitrogen gas. At this time, gas chromatography shows that the starting perfluoroalkyl iodide is consumed. The product is washed two times with water (~150 g per wash). To the resultant orange semi-solid is added sodium hydroxide (50%, 37.6 g, 0.47 mol) and 120.0 g H$_2$O. This mixture is heated at 80° C. with stirring for 16 hours, followed by neutralization with 10% hydrochloric acid and two water washes (~120 g per wash). To remove any residual water, the product is azeotroped with toluene. The toluene is vacuum distilled, yielding a tan waxy solid.

By NCO titration, the hydroxy value is found to be 1353 (theoretical, 1060). Fluorine analysis shows the product to be 55% F, 92% of theory.

Example 10

Synthesis of 2-propylsulfate, 1,3-bis((perfluoro-C$_{6-18}$alkyl-2-propenyl)oxy)-, ammonium salt Into a 50 ml three neck round-bottomed flask is placed 15 g (0.014 mol) of 2-propanol, 1,3-bis((perfluoroC$_{6-18}$alkyl-2-propenyl)oxy)-, along with 5.3 g (0.055 mmol) of sulfamic acid and 1.4 g (0.0166 mol) pyridine. It is then heated at 100° C. for 6 hours. The final product is a brown, hard solid containing 44.3% F.

$^1$H-NMR (500 MHz, CDCl$_3$) d3.8 (CHOCH$_{2,4}$Hm), 4.2 (OCH$_2$CH,4Hdd), 4.7 (OCHCH$_2$,quin), 5.9 (CH$_2$CCH=, 2H,dd), 6.4 (R$_F$CH,2H,m).

Examples 11–13

Using the methods described in Examples 1–9, the following additional perfluoroalcohols are prepared:

| Example | Perfluoroalkyl-alcohol |
|---|---|
| 11 | (C$_6$F$_{13}$CH=CHCH$_2$OCH$_2$)$_n$—C(CH$_2$OH)$_{4-n}$ n = 2,3 |
| 12 | (C$_6$F$_{13}$CH=CHCH$_2$OCH$_2$)$_2$C(C$_2$H$_5$)CH$_2$OH |
| 13 | (C$_8$F$_{17}$CH=CHCH$_2$OCH$_2$)$_2$CHOH. |

Example 14

Synthesis of a di-(2-hydroxy-4-oxa-6,7-ene-7-perfluoroalkyl)-thioether

A 150 ml three-necked, round-bottomed flask is charged with 19.2 g (0.08 mol, 98%) sodium sulfide nonahydrate and 60 g deionized water. The solution is heated to 42° C and 18.2 g (0.16 mol) allyl glycidyl ether is added over a one hour period to give a cloudy solution. The reaction mixture is heated at 60° C. for one hour. The product mixture is concentrated on a rotary evaporator with reduced pressure at 70° C. to give a slightly viscous, clear, brown oil in 88% yield (18.3 g). Analytical data: $^1$H NMR (500MHz, CDCl$_3$) d: 2.50–2.70 (4H, m, —CH$_2$S—), 3.71 and 3.72 (8H, M —OCH$_2$CHOH— and CH$_2$=CHCH$_2$—) 3.87 (2H, m, —CH$_2$CHOHCH$_2$O, 5.00 and 5.14 (4H, dd, CH$_2$=CH—), 5.80 (2H, m, CH$_2$=CHCH$_2$).

8.4 g (0.032 mol) of this thio ether secondary diol, 38.0 g (0.063 mol) perfluoroalkyl iodide with a homologue distribution of 1.7% C$_6$, 49.8% C$_8$, 33.5% C$_{10}$, 11.1% C$_{12}$, 3.1% C$_{14}$, 0.69% C$_{16}$ and 0.16% C$_{18}$ (TEL-AN, from Du Pont), 0.3 g (1.90mmol) AIBN, and 1.2 g (0.006 mol) sodium metabisulfite is stirred under nitrogen gas at 70° C. in a three-necked, round-bottomed flask. After 1.5 hours, the reaction is complete based on gas chromatography.

Dehydrohalogenation is performed by the addition of 25.2 g (0.32 mol, 50%) sodium hydroxide. The mixture is stirred at 90° C. for 20 minutes to allow for completion. The aqueous layer is removed and the organic layer is taken up in 150 ml 2-pentanone. After 2 successive washes with 100 ml deionized water each, the solvent is stripped off on a rotary evaporator under reduced pressure to give a yellow solid in a yield of 32.0 g(83.4%). $^1$H NMR (500 MHz, CDCl$_3$) d: 2.7 and 2.8 (4H, m, —CH$_2$S—), 3.5 (4H, m, OCH$_2$CHOH—, 3.95 (2H, m, —CH$_2$CHOHCH$_2$—), 4.2 and 4.35 (4H, m, —CH$_2$CH$_2$O—, cis/trans coupling with olefinic hydrogens), 5.6 and 5.9 (2H, m, CF$_2$CH=CH—), 6.3 and 6.45 (2H, m, —CH=CH=CH$_2$—). The product contains 71% trans isomer as determined from integration.

Example 15

Synthesis of a di-(2-hydroxy-4-oxa-6,7-ene-7-perfluoroalkyl)-butylamine

Distilled n-butylamine (10.0 g, 0.137 mol) is dissolved in 30 g deionized water in a three-necked, 250 ml round-bottomed flask. The solution is heated to 40° C. and 31.3 g (0.274 mol) allyl glycidyl ether is charged over 30 minutes; the temperature of the mixture spontaneously rises to 60° C. and is maintained there for 6 hours. After this time the product is concentrated at reduced pressure on a rotary evaporator to give a clear, yellow liquid in 98% yield (40.4 g). Analytical data: $^1$H NMR (500 MHz, CDCl3) d: 5.8 (2H, m, CH$_2$=CH—), 5.2 (2H, dd, CH$_2$=CH—, trans), 5.1 (2H, dd, CH$_2$=CH—, cis), 3.9 (4H, t, —CHCH$_2$O—), 3.8 (2H, bs, —CH$_2$CHOHCH$_2$—), 3.4 (4H, m, —OCH$_2$CHOH—), 2.5(4H, m, =CHOHCH$_2$N— and 2H, m, =NCH$_2$CH$_2$), 1.4(2H, quintet, —CH$_2$CH$_2$CH$_2$), 1.2 (2H, sextet, —CH$_2$CH$_3$), 0.8 (3H, t, —CH$_2$CH$_3$).

11.7 g (0.039 mol) of the above diallyloxy-butylamine diol, 47.0 g (0.078 mol) perfluoroalkyl iodide with a homologue distribution of 1.7% C$_6$, 49.8% C$_8$, 33.5% C$_{10}$, 11.1% C$_{12}$, 3.1% C$_{14}$, 0.69% C$_{16}$ and 0.16% C$_{18}$, 1.5 g (0.008 mol) sodium metabisulfite, and 14 g deionized water are charged into a 250 ml three-necked, round-bottomed flask. Under nitrogen, the biphasic mixture is heated to 70° C. and a charge of 0.63 g (3.92 mmol) azo-bisisobutyronitrile (AIBN) is made. A temperature rise of 11° C. is noted. Once cooled back to 70° C., the reaction mixture is allowed to go to completion. This takes 1.5 hours as determined by gas chromatography.

Dehydrohalogenation is carded out by the addition of 12.8 g (0.16 mol, 50%) sodium hydroxide. The mixture is stirred at 90° C. for 3 hours. The aqueous layer is removed and the organic layer is washed three times with 200 ml slightly alkaline, deionized, water. The final product is isolated as a brown, thick syrup in 88.6% yield (43.2 g). Analytical data: $^1$H NMR (500 MHz, CDCl3) d: 6.5 (2H, d, —CF$_2$CH$_2$=CH-trans coupling), 6.3 (2H, m, —CF$_2$CH=CH—, cis coupling), 5.9 (2H, m, CF$_2$CH=CH—, trans coupling), 5.6 (2H, m, —CF$_2$CH=CH—, cis coupling), 4.1 (4H, bs, —CH=CH—CH$_2$), 3.9 (2H, m, —CH$_2$CHOHCH$_2$—), 3.5 (4H, m, —OCH$_2$CHOH—), 2.6 (4H, m, =CHOHCH$_2$N— and 2H, t, —CH$_2$CH$_2$N—), 1.4 (2H, quintet, —CH$_2$CH$_2$CH$_2$—), 1.3 (2H, sextuplet, —CH$_2$CH$_2$CH$_3$), 0.9 (3H,t, —CH$_2$CH$_3$). The product contains 72% trans isomer as determined from integration.

Example 16

Synthesis of a di-R$_F$-diacid: preparation of R$_F$-allyl glycidyl ether adduct with ethylenediamine diacetic acid 51.45 g (0.0850 moles) R$_F$-iodide with a chain length distribution as in Example 3 (TEL AN, from DuPont), 15.0 g water and 10.00 g (0.0850 moles) allyl glycidyl ether are weighed into a 250 ml 3-neck round-bottomed flask equipped with a mechanical stirrer, nitrogen inlet, thermometer and condenser. The reaction mixture is heated to 80° C. while stirring and 0.33 g (0.0017 moles) 2,2'-azo-bis-(2-methylbutyronitrile) (VAZO-67, from WAKO Chem. Co.) are added. An additional 0.16 g (0.00083 moles) VAZO 67 are added after two hours and another 0.48 g (0.0025 moles)of VAZO 67 after four hours. The reaction is continued for five hours at 65° C. A subsequent GC scan shows only a minute amount of R$_F$-iodide remaining. To this mixture are added 55.42 g (0.0425 moles) commercial ethylenediamine diacetic acid sodium salt solution (16.88% actives by amine titration) and 2 g 50% NaOH. The reaction temperature is raised to 90° C. and the mixture is stirred for 5 hours. 5 g 50% NaOH and 10 g 1-propanol are added and the reaction mass is kept at 93° C. for 10 hours. To effect dehydrohalogenation, 15 ml 50% NaOH are added and the reaction mixture is stirred at 93° C. for 14 hours. The mixture is transferred to a 1000 ml Erlenmeyer flask and 500 g water and enough acetic acid are added to reduce the pH to 3; then the mixture is cooled with an ice bath. The precipitate is filtered off and dried under vacuum. Yield is 71% (by weight). Elemental analysis: 29.9% C, 2.0% H and 1.6% N (theoretical: 32.1 C%, 2.21% H and 2.06% N).

For application testing the acid is neutralized with NaOH and dissolved in water.

Example 17

The following examples describe the synthesis of polyurethanes.

40.17 g (31.4 mmoles) of the diol of example 14 and 86.27 g isopropyl acetate are placed in a 250 ml 3-necked round-bottom flask fitted with a mechanical stirrer, gas inlet, thermometer, Dean-Stark trap and condenser. The system is kept under nitrogen and heated to reflux to remove water as an azeotrope with isopropyl acetate: 18 ml of distillate are collected in the trap. The contents are cooled to 75° C. and 5.03 g (23.6 mmoles) of 2,2,4-trimethyl-1,6-diisocyanatohexane (TMDI) are added followed by 0.10 g (0.16 mmoles) dibutyltin dilaurate (DBTL). The contents are stirred at 80° C. until the TMDI content is 0.5% as determined by IR (6 hrs). 11.57 g (19.5 mmoles) of Dimer Acid Diisocyanate (DDI 1410, (from Henkel Chemie) and 1.45 g (12.2 mmoles) of N-methyl diethanolamine (NMDEA) are added, followed by 16.3 g isopropyl acetate as a rinse. The mixture is stirred for 6 hours at 80° C. After this time no more NCO groups remain present as determined by IR-spectroscopy. The product polyurethane is obtained as a 40% solution in isopropyl acetate and contains the diol of Ex. 14, TMDI, DDI, and NMDEA in a mol ratio of 4:3:2.5:1.5. On drying the polyurethane forms a tough clear film.

Examples 18 and 19

Following the procedure of Example 17, polyurethanes are prepared from the $R_F$-diols of Examples 14 and 15; their compositions and properties are listed in the table below.

Example 20

Synthesis of a polyurethane from the allylether-substituted oligo-ethyleneoxide diol of Example 9.

In a 250 ml 3-necked round-bottomed flask fined with a mechanical stirrer, gas inlet, thermometer, Dean-Stark trap and condenser are placed 40.29 g (25.5 mmoles) of the oligoether diol of Example 9 and 118.37 g isopropyl acetate. The system is kept under nitrogen and heated to reflux to remove water as an azeotrope with isopropyl acetate: 18.3 ml of distillate are collected in the trap. The contents are cooled to 75° C., and 24.34 g (41.1 mmoles) of Dimer Acid Diisocyanate (DDI 1410, (from Henkel Chemie) are added followed by 0.10 g (.16mmoles) dibutyltin dilaurate (DBTL) and 1.65 g (13.8 mmoles) of N-methyl-diethanolamine (NMDEA). The contents of the flask are heated to 80° C. and stirred for 5 hours, after which time no NCO groups are present as determined by IR-spectroscopy. The product polyurethane is obtained as a 40% solution in isopropyl acetate. It contains the diol of Example 2, DDI, and NMDEA in a mol ratio of 1:1.5:0.5.

Example 21 a–d

The polyurethane solutions were diluted with isopropyl acetate to 1% solids and coated onto glass microscope slides, which were air dried and heated for ten minutes at 60° C. before measuring contact angles of water and decane. The results show that the coatings are both water- and oil-repellent.

| EX. 21- | diol of EX. | Composition, mol ratio of $R_F$-diol/TMDI/DDI/NMDEA | Contact angles | |
|---|---|---|---|---|
| | | | water | decane |
| a | 14 | 4:3:2.5:1.5 | 106 | 66 |
| b | 15 | 4:3:2.5:1.5 | 104 | 49 |
| c | 9 | 4:3:2.5:1.5 | 108 | 61 |
| d | 15 | 1:0:1.5:0.5 | 110 | 65 |

Example 22

This example illustrates the synthesis of a di-perfluoroalkylsulfate ester ammonium salt by reaction with sulfamic acid.

Into a 100 ml round-bottomed flask are placed 1-propanol, 3-(perfluoro$C_{6-18}$alkyl- 2-propenyl)oxy)-2,2-bis-((perfluoro$C_{6-18}$alkyl-2-propenyl)oxy)methyl)—(from Example 4), (16.46 g, 0.01 mol), sulfamic acid (1.78 g, 0.018 mol) and 3.33 g tetramethylurea. This mixture is stirred under nitrogen for 1.5 hours at 103° C. Progress of the reaction and the final degree of sulfation are monitored by a two-phase titration of the formed bisperfluoroalkylsulfate ammonium salt with benzothonium chloride solution according to the procedure described in, "Analysis of Surfactants", Surfactant Sci. Series, Vol. 40, (Marcel Dekker, Inc., New York, 1992).

The final degree of sulfation, expressed as OH equiv. initial —OH equiv. final, is 0.9.

The product is dissolved in water and used for application tests.

Examples 23–25

Following the procedure of Example 22, the $R_F$-alcohols of Examples 3 and 6, and the $R_F$-diol of Example 9 are reacted with sulfamic acid, with the degrees of sulfation indicated:

| Example No. | $R_F$compound of Ex. No. | Degree of Sulfation |
|---|---|---|
| 22 | 4 | 0.9 |
| 23 | 3 | 0.95 |
| 24 | 6 | 0.85 |
| 25 | 9 | 1.0 |

Example 26

The following example shows the performance of the novel sulfate acids and carboxylic acid salts, as well as of 11-perfluoroalkyl-10-undecenoic acid salts as internal and external paper sizes.

SAMPLE PREPARATION AND TESTING

The required amounts of 2% solutions of the test compounds in distilled water are dissolved in enough aqueous ammonia to achieve complete neutralization of the acid groups; the pH of the resulting solutions or dispersions is 9 to 9.5. Samples of the fluorochemicals are then diluted to the test application levels with distilled water.

1. External Size Application

The neutralized test solutions are added to a 4% aqueous solution of paper maker's starch (Stayco M, oxidized starch, from Staley Corp.) and then applied to unsized paper by padding (paper dipped through starch solution, and passed through single nip rollers). The resulting sheets are dried at ambient conditions for 15 minutes, then 3 minutes at 200° F. in an "Emerson Speed Drier" (heated metal plate with canvas cover).

Oil Kit Test

The oil repellency of the surface is determined by using the TAPPI UM 557 OIL KIT TEST, which consists of determining with which of twelve castor oil-heptane-toluene mixtures having decreasing surface tension penetration occurs within 15 seconds; ratings go from 1, lowest, to 12.

Grease Resistance Test

Grease resistance is determined with the Ralston-Purina test for pet food materials; RP-2 Test, Ralston-Purina Company, Packaging Reference Manual Volume 06—Test Methods.

In summary: cross-wise creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Ratings are determined by the percentage of stained grid segments, using at least two samples.

2. Internal Size Application and Testing

Six grams of dry recycled pulp consisting of 70% hardwood and 30% soft-wood are diluted in 289 ml distilled water and thoroughly dispersed in a blender. To this pulp slurry is added the required amount of a 1% solution of the test compound in distilled water and mixed in for 5 minutes. Then 6 ml of a 1% aqueous solution of cooked cationic starch are added and mixed together for an additional 5 minutes. To this mixture 24 ml of a 50% (on solids) dilution of a water-repellent adjuvant (Hercon-76, from Nalco Chem. Corp.) are added and mixed in for another 10 minutes. The resulting slurry is diluted with an additional 500 ml of distilled water and mixed again. This mixture is then poured over a 100 mesh wire screen, with a vacuum applied from below which pulls the water from the pulp mixture to form a sheet on the screen. The wet sheet is removed from the screen and dried between another screen and hard surface at a pressure of approximately 0.4 lb./in$^2$ at 110° C. for 1½ hours.

Hot-Oil Test

One ml of hot (110° C.) corn oil is placed on the paper and the time is recorded for penetration to occur (20 minutes maximum). Paper made in the same manner, including the cationic starch and water-repellent adjuvant, but without a fluorochemical, demonstrates an oil kit number of <1 and holds the hot corn oil for less than one minute (begins to penetrate as soon as applied). The amount of oil absorbed is determined gravimetrically by weighing the paper before and after the hot-oil test, and after the surface oil has been removed.

The Oil-Kit Test is the same as that for the External Size.

Hot-Water Test

One ml of a hot (83° C.) 5% lactic acid solution is placed on the paper plate, and hold-out time and absorption are measured the same way as in the hot-oil test.

The test results are shown in the following table.

| $R_F$-salt of Ex. No. | % F | External Size | | Internal Size | | % OIL AB-SORBED |
|---|---|---|---|---|---|---|
| | | OIL KIT | RP-2 | OIL KIT | HOLD OUT TIME (MIN) | |
| 24 | 0.05 | 0 | 2 × 100 | 2 | <1 | 94 |
| | 0.07 | 0 | 2 × 100 | 2 | <1 | 93 |
| | 0.1 | 4 | 5, 5 | 3 | >20 | 30 |
| 23 | 0.05 | 3 | 2 × 0 | 2 | >20 | 7 |
| | 0.07 | 5 | 2 × 0 | 4 | >20 | 5 |
| | 0.1 | 7 | 2 × 0 | 5 | >20 | 2 |
| 22 | 0.05 | 4 | 2 × 0 | 2 | >20 | 7 |
| | 0.07 | 5 | 2 × 0 | 4 | >20 | 0 |
| | 0.1 | 6–7 | 2 × 0 | 5 | >20 | 0 |
| 25 | 0.05 | 5 | 2, 40 | 6 | >20 | 3 |
| | 0.07 | 7 | 2 × 0 | 8 | >20 | 6 |
| | 0.1 | 10 | 2 × 0 | 10 | >20 | 5 |
| 16 | 0.05 | | | 2 | 1 | 100 |
| | 0.07 | | | 4 | 20 | 2 |
| | 0.1 | | | 5 | >20 | 3 |

Example 27

Synthesis of N,N-(2-hydroxy-4-oxa-7-perfluoroalkyl-6,7-heptenyl)-aspartic acid a) Synthesis of a diallyl-diacid from aspartic acid and allyl glycidyl ether A mixture of 29.3 g (0.22 mol) aspartic acid, 35.2 g (0.44 mol, 50%) sodium hydroxide, 35 g deionized water, and 30 g n-propanol is stirred at 50°–55° C. in a three-necked, round-bottomed flask equipped with condenser, dropping funnel and stirrer, 50.2 g (0.44 mol) allyl glycidyl ether are added over 50 minutes to give a cloudy, biphasic system which after an additional hour at 50° C. becomes clear and homogeneous. The reaction mixture is then stirred for an additional 4 hours at 50°–55° C. Complete consumption of the epoxide is ascertained by gas chromatography.

b) Addition of $R_F$-iodide

At 30° C., 265 g (0.44 mol) perfluoroalkyl iodide with a homologue distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$ (TEL-AN, from DuPont), 1.7 g (0.0088 mol) VAZO-67, and 4.2 (0.022 mol) sodium metabisulfite are charged to the above mixture under a nitrogen purge. The slightly yellow, milky mixture is then heated to 75° C.; the temperature rises to 88° C. After cooling back to 75° C., the white, pasty mixture is stirred for an additional 260 minutes. At this time the $R_FI$ is completely consumed. A charge of 36.5 g (0.46 mol, 50%) sodium hydroxide is slowly added to the mixture to eliminate HI. After 40 minutes the product mixture is cooled to room temperature and poured into 3000 ml cold, deionized water. The mixture is neutralized with dilute HCl to pH 2–2.5, filtered and washed. Drying is carried out using 25 mm Hg vacuum at 50° C. for 2 days to yield 270 g (94% yield) of off-white powder.

Example 28

1). Synthesis of N,N-(2-hydroxy-4-oxa-7-perfluoroalkyl-6,7-heptenyl)-1,1-dihydroxymethylaminopropane a) Allyl glycidyl ether addition to amine

A solution of 42.0 g (0.35 mol) 2-amino-2-ethylpropanediol and 39.7 g distilled water is stirred at 25° C. in a three-necked, round-bottomed flask equipped with a condenser, dropping funnel and stirrer. 83.2 g (0.73 mol) allyl glycidyl ether are added over 60 minutes to give a clear solution. An additional 1.4 g (0.01 mol) 2-amino-2-ethylpropanediol are added and the clear solution is stirred 4 hours at 25° C., followed by one hour at 80° C. Complete consumption of the epoxide is ascertained by gas chromatography.

b) $R_F$-I addition

At 25° C., 101.4 g (0.17 mol) perfluoroalkyl iodide with a homologue distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$ (TEL-AN, from DuPont), 3.2 g (0.02 mol) sodium metabisulfite and 39.5 g distilled water are charged to a three-necked, round bottomed flask equipped with a condenser and stirrer under a nitrogen purge. The slightly yellow mixture is then heated to 85° C. and 49.1 g (0.9 mol) of the above solution together with 0.715 g (0.004 mol) Vazo 67 are added. The mixture is stirred at 85° C. for 4 hours. At this time $R_F$I is completely consumed. A charge of 4.35 g (0.11 mol) sodium hydroxide dissolved in 9.1 g distilled water is slowly made over 15 minutes to eliminate HI. After 6.5 hours at 85° C., 30.5 g distilled water and 5.5 g isopropanol are added. The contents form two layers when agitation is stopped. The bottom organic layer is washed twice with 25 ml hot water; then dried under 25 inches Hg vacuum at 70° C. for 7 hours to yield 51.0 g (45.5%) of a brown solid.

the middle layer, which is separated and filtered. A brown paste is obtained, which is dried under 25 inches Hg vacuum at 100° C. for 7 hours to yield a brown solid in 95% yield.

Example 29

45.74 g (0.0756 moles) $R_F$-iodide with a $R_F$-chain length distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$, (TEL-AN, from DuPont), 23.23 g distilled water, 0.75 g (0.004 moles) sodium metabisulfite and 15.27 g (0.083 moles) 10-undecylenic acid ($C_{11}$-A) are placed in a 100 mol 3-necked round bottom flask equipped with stirrer, condenser, gas inlet tube and thermometer. The mol ratio of $R_F$-I/$C_{11}$-acid is 1/1.09. The mixture is stirred and sparged with nitrogen and 1 g dry ice, then heated to 80° C. Next 0.0239 g (0.13 mmoles) 2,2'-azobis-(2-methylbutyronitrile) (VAZO 67) are added, followed by 0.026 g VAZO-67 after 3 hours and 0.033 g VAZO 67 after 7 hours. The progress of the reaction is monitored by observing the disappearance of $R_F$I by gas chromatography.

After 9 hours reaction time, 20.0 g of a 50% NaOH solution are added. The mixture is stirred at 70° C. for 3 hours; then is cooled to room temperature. The mixture is slowly poured into 1 liter of ice water acidified with 100 g of a 10% hydrochloric acid solution. The precipitate is filtered, washed several times with cold water and dried in vacuo to a tan, waxy solid with a melting point of 43°–54° C. The yield is 48 g (93% of theory.).

Example 30

The products of examples 27–30 are dispersed in water and the pH of the dispersions are adjusted to 9; the resulting solutions and dispersions are used as internal and external paper sizes and the samples are tested as previously described. The following table shows the test results.

| Product of Ex. No. | % F | External Size OIL TEST | | Internal Size OIL TEST | | | WATER TEST | |
|---|---|---|---|---|---|---|---|---|
| | | OIL KIT | RP-2 | OIL KIT | OIL HOLD OUT (MIN) | % OIL ABSORB. | WATER HOLD OUT (MIN) | % WATER ABSORB. |
| 27 | 0.05 | 6 | 4 × 0 | 3 | >20 | 4 | >20 | 4 |
|    | 0.07 | 8 | 4 × 0 | 3 | >20 | 3 | >20 | 3 |
|    | 0.1  | 10 | 4 × 0 | 4 | >20 | 4 | >20 | 4 |
| 28 | 0.05 | 5 | 4 × 0 | 3 | <1  | 96 | >20 | 2 |
|    | 0.07 | 6 | 4 × 0 | 3 | >20 | 13 | >20 | 4 |
|    | 0.1  | 8 | 4 × 0 | 4 | >20 | 2  | >20 | 3 |
| 29 | 0.05 | 4 | 2 × 100 | 3 | >20 | 0 | >20 | 7 |
|    | 0.07 | 6 | 2 × 100 | 4 | >20 | 8 | >20 | 7 |
|    | 0.1  | 7 | 2 × 100 | 4 | >20 | 10 | >20 | 5 |

2). Phosphation

At 25° C., 12.04 g C$_{001}$ mol) of the amine tetrol of part 2.), 5.99 g polyphosphoric acid and 4.17 g glyme are charged to a three-necked, round bottomed flask equipped with a condenser and stirrer and using a nitrogen purge. The mixture is then heated to 90° C. for 3.5 hours to give a brown viscous mixture. Then 20 g methyl propyl ketone, 20 g distilled water and 13 g conc. HCl are added and the mixture is stirred until it is homogeneous at room temperature. Then the stirrer is stopped and the contents are allowed to settle out into three layers. The major component is contained in

Example 31

Synthesis of a di-$R_F$-amino-diacid

A mixture of 13.2 g (89.7 mmol) glutamic acid, 16.0 g (200 mmol, 50%) sodium hydroxide, 16 g deionized water, and 12 g n-propanol is stirred at 50°–55° C. in a three-necked, round-bottomed flask equipped with condenser, dropping funnel, and stirrer. Then 20.0 g (175 mmol) allyl glycidyl ether are added over 20 minutes to give a cloudy, biphasic system which, after and additional hour at this temperature, becomes clear and homogeneous. The reaction mixture is stirred for an additional 5 hours at 50°–55° C.; then taken to reflux (90° C.) for 30 minutes. Complete consumption of the epoxide is ascertained by gas chromatography.

$R_F$I Addition

At 30° C., 105.3 g (175 mmol) $R_F$I with a $R_F$-chain length distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$, (TEL-AN, from DuPont), 0.7 g (3.6 mmol) VAZO-67, and 1.7 g (9 mmol) sodium metabisulfite are charged to the above mixture under a nitrogen purge. The slightly yellow, milky mixture is then heated to 77° C. and the temperature rises to 90° C. After cooling back to 80° C., the white, pasty mixture is stirred for an additional 180 minutes. At this time the $R_F$I is completely consumed. Then 16 g (190 mmol, 50%) sodium hydroxide is slowly added to the mixture to eliminate HI. After 60 minutes, the product mixture is cooled to room temperature, poured into 3000 ml cold, deionized water and neutralized with dilute HCl to pH 2–2.5. A precipitate is formed, which is filtered and washed. After drying at 25 mm Hg at 55° C. for one day, 113 g of the product are obtained as a brown solid in 97% yield.

Example 32

Synthesis of a di-$R_F$-amino-monoacid

In a three-necked, 300 ml round-bottomed flask equipped with condenser, thermometer and mechanical stirrer are placed 12.0 g (0.0105 mmol) allyl glycidyl ether, 4.7 g (0.0526 mmol β-alanine, 4.2 g (0.0526 mmol, 50%) sodium hydroxide, 4.5 g deionized water and 3.6 g n-propanol. The two-phase mixture is stirred while the temperature is raised to 85° C. After 15 minutes at this temperature, a clear yellow, homogeneous system is formed. After 2 hours, total consumption of epoxide is determined by gas chromatography and the solution is cooled to 30° C.

To the above solution are charged 63.2 g (0.105 mmol) $R_F$I with a $R_F$-chain length distribution of 1.7% $C_6$, 49.8% $C_8$, 33.5% $C_{10}$, 11.1% $C_{12}$, 3.1% $C_{14}$, 0.69% $C_{16}$ and 0.16% $C_{18}$, (TEL-AN, from DuPont), 1.0 g (5.26 mmol) sodium metabisulfite, and 0.4 g (2.10 mmol) VAZO-67. The mixture is heated under nitrogen to 75° C. and continues to rise to 90° C. The flask contents are cooled down to 85° C. and stirred at this temperature for 4 hours. All the $R_F$I is used up as determined by GC. 12 g (0.105 mmol, 50%) sodium hydroxide is added to eliminate HI and the mixture is stirred for an additional hour. The product mixture is then poured into one liter of cold water and acidified with 10% hydrogen chloride. A precipitate is formed which is filtered and dried, first in air at room temperature and then under vacuum to give 63.9 g (96% yield) of a light tan solid.

Example 33

The procedure of example 32 is repeated, but using instead of beta-alanine an equivalent amount of taurine (2-aminoethylenesulfonic acid). The resulting di-$R_F$-amino-sulfonic acid is obtained in 91% yield as a light tan solid, which is soluble in aqueous ammonia.

What is claimed is:

1. An oligo-perfluoroalkyl alcohol or acid of the formula I or II $$(Q_F\text{—}CH_2O)_b\text{—}Y\text{—}(X)_a \quad (I)$$

or $$Z_e(\text{—}L\text{—}(U\text{—}OH)_d)_c \quad (II)$$

wherein $Q_F$ is $Q_{F1}$ or $Q_{F2}$, in which $Q_{F1}$ is $R_FCH_2CHI$— and $Q_{F2}$ is $R_FCH=CH$—, and $R_F$ is a monovalent, perfluorinated, alkyl or alkenyl, straight, branched or cyclic organic radical having three to twenty fully fluorinated carbon atoms, which radical can be interrupted by divalent oxygen or sulfur atoms, with each $R_F$ radical being identical or different from the other $R_F$ radicals, Y is a trivalent or tetravalent organic linking group with from 1 to 20 carbon atoms, which can be interrupted by one or more polyvalent groups or hetero atoms selected from —O—, —S—, —N<, —NR$_1$—, —CO—, —CONR$_1$—, —NHCOO—, —CON<, —CO$_2$—, —O$_2$C—, —O$_2$CO— and —SO$_2$—, in which $R_1$ is hydrogen, $C_1$–$C_{20}$alkyl, di-$C_1$–$C_2$alkylamino-$C_2$–$C_6$alkylene, hydroxy-$C_1$–$C_5$alkylene, or $C_1$–$C_5$alkyl or hydroxy-$C_1$–$C_5$alkylene, which is substituted by pyridyl, piperidyl or cyclohexyl.

X is OH, O—CH$_2$—COOH or COOH, a is 1 or 2, b is 2 or 3,

L is O, S or NR', in which

R' is $C_1$–$C_{20}$hydrocarbyl, hydroxy-$C_2$–$C_5$alkylene, carboxymethylene or U—OH, U is CH$_2$—CH—(O—CH$_2$—CH)$_r$—(O—CH$_2$—CH)$_q$
       |             |             |
     CH$_2$OCH$_2$Q$_F$  CH$_2$OCH$_2$Q$_F$  CH$_2$OCH=CH$_2$, Z is H or a mono-, di-, tri- or tetravalent organic group of 1–40 carbon atoms which can be interrupted by one or more polyvalent groups or hetero atoms selected from —O—, —S—, —N<, —NR$_1$—, —CO—, —CONR$_1$—, —NHCOO—, —CON<, —CO$_2$—, —O$_2$C—, —O$_2$CO— and —SO$_2$—, and can also be substituted by hydroxyl, carboxyl, carboxyalkyl or sulfonate when L is S or NR', r and q are each, independently, 0 to 10, c is 1 to 4, d is 1 to 3, with the proviso that when c and d are both 1, Z is monovalent and r is >0, and e is 0 or 1, with the proviso that when e is 0, d is 2 and L is S or NR'.

2. A compound of the formula I or II according to claim 1, wherein $Q_F$ is $Q_{F2}$ and $R_F$ is saturated, contains 6–18 carbon atoms, is fully fluorinated and contains at least one terminal perfluoromethyl group.

3. A compound of the formula I or II according to claim 2, wherein $R_F$ is a fully fluorinated, linear carbon chain with 6 to 14 carbon atoms.

4. A compound of the formula I according to claim 1, wherein Y is a trivalent or tetravalent hydrocarbyl linking group with from 1 to 10 carbon atoms.

5. An alcohol of the formula I according to claim 2, which is selected from the group consisting of $(Q_{F2}CH_2OCH_2)_2CHOH$, $(Q_{F2}CH_2OCH_2)_2C(CH_2OH)_2$, $(Q_{F2}CH_2OCH_2)_3C$—$CH_2OH$ and $(Q_{F2}CH_2OCH_2)_2C(C_2H_5)CH_2OH$.

6. An acid of the formula I according to claim 1, which is selected from the group consisting of

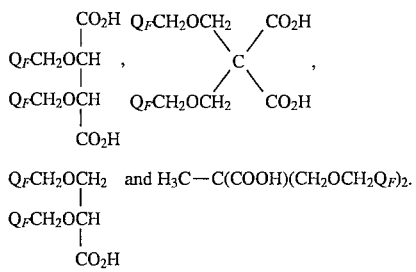

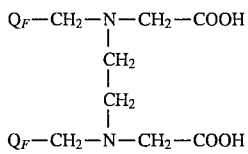

7. An acid of the formula $$Q_F-CH_2-N-CH_2-COOH$$
$$|$$
$$CH_2$$
$$|$$
$$CH_2$$
$$|$$
$$Q_F-CH_2-N-CH_2-COOH$$

where $Q_F$ is $Q_{F1}$ or $Q_{F2}$, in which $Q_{F1}$ is $R_FCH_2CHI-$ and $Q_{F2}$ is $R_FCH=CH-$, and $R_F$ is a monovalent, perfluorinated, alkyl or alkenyl, straight, branched or cyclic organic radical having three to twenty fully fluorinated carbon atoms, which radical can be interrupted by divalent oxygen or sulfur atoms, with each $R_F$ radical being identical to or different from the other $R_F$ radicals.

8. A compound of the formula II according to claim 2, wherein r is equal to or greater than q and the sum of r plus q is 0 to 10.

9. A compound according to claim 8, wherein r is is equal to or greater than q and is 0 to 5 and q is 0 to 3.

10. A compound of the formula II according to claim 2, wherein L is O and a) c and d are 1 and Z is phenyl, carboxyphenyl, p—n—$C_1$–$C_{10}$alkylphenyl, a monovalent alkyl or alkenyl radical with 1–20 carbon atoms which may be interrupted by —O—, —S— or —$NR_1$— groups, and may be substituted by one or two carboxyl groups, or is hydroxy-$C_2$–$C_5$alkylene, or b) c is 2, d is 1 and Z is 1,4-phenylene or a divalent alkylene radical which may be interrupted by —O—, —S— or —$NR_1$— groups and substituted by one or two carboxyl groups, or c) c is 3, d is 1 and Z is a trivalent alkylene radical which may be interrupted by —O—, —S— or —$NR_1$— groups, or d) c is 4, d is 1 and Z is a tetravalent residue of a polyol.

11. A compound of the formula II according to claim 2, wherein L is S and a) d is 2 and Z is either a direct bond if e is 1 or e is 0, or b) d and c are 1 and Z is a monovalent linear or branched alkyl radical with 1–20 carbon atoms, hydroxy-$C_2$–$C_5$alkylene, carboxy—$C_2$–$C_4$alkylene or —CH(COOH)$CH_2$COOH, or c) d is 1, c is 2 and Z is a divalent $C_2$–$C_{20}$alkylene radical which may be interrupted by —O— or —$NR_1$—.

12. A compound of the formula II according to claim 2, wherein L is NR', wherein R' is U—OH, $C_1$–$C_5$alkyl or carboxymethylene, c, d and e are each 1 and Z is monovalent.

13. A compound of the formula II according to claim 12, wherein R' is U—OH and Z is a monovalent alkyl radical with 1–20 carbon atoms which may be interrupted by —O—, —S— or —$NR_1$— groups or a phenyl radical, which radicals may be substituted by hydroxy, carboxy or sulfonate groups.

14. A compound of the formula II according to claim 13, wherein Z is the residue minus 1 $NH_2$ radical of butylamine, aminoethanol, 1,1-dihydroxymethylaminopropane, tris(hydroxymethyl)aminomethane, glucamine, p-aminobenzoic acid, beta-alanine or HOOC—CH($NH_2$)—A, wherein A is the radical residue of an a-amino acid selected from glycine, alanine, aspartic acid, glutamic acid and taurine.

15. A compound of the formula II according to claim 13, wherein Z is HOOC—$CH_2CH_2$—, HOOC—$CH_2$—, HOOC—CH($CH_3$)—, —$CH_2CH_2SO_3H$, —CH(COOH)—($CH_2$)$_{1-2}$COOH, —C($C_2H_5$)($CH_2OH$)$_2$ or ($CH_3$)$_2$N($CH_2$)$_3$—.

16. A compound of the formula II according to claim 12, wherein c is 2 to 4, d is 2 and R' is U—OH, or d is 1, R' is alkyl with 1–5 carbon atoms or a carboxymethylene group and Z is a divalent alkylene radical with 2 to 12 carbon atoms which be interrupted by —O—, —S— or —$NR_1$— groups and substituted by hydroxy, carboxy or sulfonate groups.

17. A compound of the formula II according to claim 16, wherein Z is the diradical residue (minus 2 $NH_2$ or $NHR_1$ groups) of 1,3-diaminopropane, 1,3-diamino-2-hydroxypropane, 2-(2-aminoethylamino)-ethanol, N,N'-bis(2-hydroxyethyl)-ethylenediamine, ethylenediamine diacetic acid or lysine.

18. An alcohol of the formula II according to claim 2, which is selected from the group consisting of ($Q_{F2}CH_2OCH_2CH(OH)CH_2$)$_2$N—C($CH_2OH$)$_2C_2H_5$,
($Q_{F2}CH_2OCH_2CH(OH)CH_2$)$_2$S,
($Q_{F2}CH_2OCH_2CH(OCH_2CH_2OH)CH_2$)$_2$S and
$Q_{F2}CH_2OCH_2CH(OH)CH(OH)CH_2OCH_2Q_{F2}$.

* * * * *